(12) United States Patent
Sharma et al.

(10) Patent No.: US 10,065,044 B2
(45) Date of Patent: *Sep. 4, 2018

(54) MOLDED HEADERS FOR IMPLANTABLE SIGNAL GENERATORS, AND ASSOCIATED SYSTEMS AND METHODS

(71) Applicant: Nevro Corporation, Redwood City, CA (US)

(72) Inventors: Vivek Sharma, San Ramon, CA (US); Jon Parker, San Jose, CA (US); Yougandh Chitre, Santa Clara, CA (US); Andre B. Walker, Monte Sereno, CA (US)

(73) Assignee: Nevro Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/981,463

(22) Filed: Dec. 28, 2015

(65) Prior Publication Data

US 2016/0256696 A1 Sep. 8, 2016

Related U.S. Application Data

(63) Continuation of application No. 14/268,575, filed on May 2, 2014, now Pat. No. 9,227,076.

(Continued)

(51) Int. Cl.
*A61N 1/375* (2006.01)
*A61N 1/378* (2006.01)
*A61N 1/372* (2006.01)

(52) U.S. Cl.
CPC .......... *A61N 1/3787* (2013.01); *A61N 1/375* (2013.01); *A61N 1/3752* (2013.01);

(Continued)

(58) Field of Classification Search
None
See application file for complete search history.

(56) References Cited

U.S. PATENT DOCUMENTS

| 3,871,382 A | 3/1975 | Mann |
| 4,071,032 A | 1/1978 | Schulman |

(Continued)

FOREIGN PATENT DOCUMENTS

| WO | WO-20080121110 | 10/2008 |
| WO | WO-2011094074 A1 | 8/2011 |

OTHER PUBLICATIONS

Supplementary European Search Report and Written Opinion for European Patent Application No. 14791140.8, Applicant: Nevro Corporation, dated Jan. 5, 2017, 7 pages.

(Continued)

*Primary Examiner* — Kennedy Schaetzle
(74) *Attorney, Agent, or Firm* — Perkins Coie LLP (57) ABSTRACT

Molded headers, implantable signal generators having molded headers, and associated systems and methods are disclosed herein. An implantable signal generator in accordance with a particular embodiment includes a can having a shell and a battery positioned at least partially within the shell. An output terminal can be operably coupled to the battery and positioned to provide electrical power to a signal delivery device. A pre-molded header having a plurality of openings can be coupled to the can, and the output terminal can be positioned at least partially within an individual opening.

13 Claims, 7 Drawing Sheets

Related U.S. Application Data (60) Provisional application No. 61/819,347, filed on May 3, 2013.

(52) U.S. Cl.
CPC ..... *A61N 1/37223* (2013.01); *A61N 1/37229* (2013.01); *Y10T 29/49002* (2015.01)

(56) References Cited

U.S. PATENT DOCUMENTS

| | | | |
|---|---|---|---|
| 4,082,097 A | 4/1978 | Mann et al. | |
| D250,719 S | 1/1979 | Jacobson et al. | |
| 4,197,850 A | 4/1980 | Schulman et al. | |
| 4,230,121 A | 10/1980 | Stanton | |
| 4,441,498 A | 4/1984 | Nordling | |
| D280,930 S | 10/1985 | Speicher et al. | |
| 4,632,117 A | 12/1986 | James | |
| 4,890,616 A | 1/1990 | Pinckaers | |
| 5,065,083 A | 11/1991 | Owens | |
| 5,144,946 A | 9/1992 | Weinberg et al. | |
| D337,820 S | 7/1993 | Hooper et al. | |
| 5,279,292 A | 1/1994 | Baumann et al. | |
| D343,901 S | 2/1994 | Anderson | |
| 5,733,313 A | 3/1998 | Barreras, Sr. et al. | |
| 5,769,877 A | 6/1998 | Barreras, Sr. | |
| 5,807,397 A | 9/1998 | Barreras | |
| 5,954,758 A | 9/1999 | Peckham et al. | |
| 6,026,328 A | 2/2000 | Peckham et al. | |
| 6,076,018 A | 6/2000 | Sturman et al. | |
| 6,115,634 A | 9/2000 | Donders et al. | |
| 6,167,303 A | 12/2000 | Thompson | |
| 6,185,452 B1 | 2/2001 | Schulman et al. | |
| 6,223,080 B1 | 4/2001 | Thompson | |
| 6,236,888 B1 | 5/2001 | Thompson | |
| 6,324,426 B1 | 11/2001 | Thompson | |
| 6,434,425 B1 | 8/2002 | Thompson | |
| 6,453,198 B1 | 9/2002 | Torgerson et al. | |
| 6,472,991 B1 | 10/2002 | Schulman et al. | |
| 6,496,729 B2 | 12/2002 | Thompson | |
| 6,553,263 B1 | 4/2003 | Meadows et al. | |
| D478,990 S | 8/2003 | Kroll | |
| 6,650,943 B1 | 11/2003 | Whitehurst et al. | |
| 6,712,772 B2 | 3/2004 | Cohen et al. | |
| 6,757,561 B2 | 6/2004 | Rubin et al. | |
| 6,871,099 B1 | 3/2005 | Whitehurst et al. | |
| 7,027,860 B2 | 4/2006 | Bruninga et al. | |
| 7,054,689 B1 | 5/2006 | Whitehurst et al. | |
| D523,144 S | 6/2006 | Wenger et al. | |
| 7,142,923 B2 | 11/2006 | North et al. | |
| 7,167,756 B1 | 1/2007 | Torgerson et al. | |
| 7,184,836 B1 | 2/2007 | Meadows et al. | |
| 7,209,792 B1 | 4/2007 | Parramon et al. | |
| 7,254,449 B2 | 8/2007 | Karunasiri | |
| 7,263,405 B2 | 8/2007 | Boveja et al. | |
| D559,987 S | 1/2008 | Strother et al. | |
| 7,330,762 B2 | 2/2008 | Boveja et al. | |
| 7,337,010 B2 | 2/2008 | Howard et al. | |
| 7,437,193 B2 | 10/2008 | Parramon et al. | |
| 7,444,184 B2 | 10/2008 | Boveja et al. | |
| 7,489,968 B1 | 2/2009 | Alexander | |
| 7,496,404 B2 | 2/2009 | Meadows et al. | |
| 7,571,002 B2 | 8/2009 | Thrope et al. | |
| 7,616,990 B2 | 11/2009 | Chavan et al. | |
| 7,620,454 B2 | 11/2009 | Dinsmoor et al. | |
| 7,636,602 B2 | 12/2009 | Baru Fassio et al. | |
| 7,641,992 B2 | 1/2010 | Howard et al. | |
| 7,650,191 B1 | 1/2010 | Lim et al. | |
| D610,261 S | 2/2010 | Strother et al. | |
| 7,682,745 B2 | 3/2010 | Howard et al. | |
| 7,769,442 B2 | 8/2010 | Shafer | |
| 7,769,462 B2 | 8/2010 | Meadows et al. | |
| 7,801,601 B2 | 9/2010 | Maschino et al. | |
| 7,801,615 B2 | 9/2010 | Meadows et al. | |
| 7,818,068 B2 | 10/2010 | Meadows et al. | |
| 7,848,812 B2 | 12/2010 | Crowley et al. | |
| 7,865,245 B2 | 1/2011 | Torgerson et al. | |
| 7,879,495 B2 | 2/2011 | Howard et al. | |
| 7,894,905 B2 | 2/2011 | Pless et al. | |
| 7,916,013 B2 | 3/2011 | Stevenson | |
| D663,035 S | 7/2012 | Smith | |
| D665,086 S | 8/2012 | Smith | |
| D665,087 S | 8/2012 | Smith | |
| 8,355,797 B2 | 1/2013 | Caparso et al. | |
| 9,227,076 B2 * | 1/2016 | Sharma ............... | A61N 1/3787 |
| 9,409,020 B2 | 8/2016 | Parker | |
| 2002/0107554 A1 | 8/2002 | Biggs et al. | |
| 2002/0193844 A1 | 12/2002 | Michelson et al. | |
| 2003/0114899 A1 | 6/2003 | Woods et al. | |
| 2003/0191504 A1 | 10/2003 | Meadows et al. | |
| 2003/0195581 A1 | 10/2003 | Meadows et al. | |
| 2003/0204222 A1 | 10/2003 | Leinders et al. | |
| 2003/0208244 A1 | 11/2003 | Stein et al. | |
| 2004/0098060 A1 | 5/2004 | Ternes | |
| 2004/0215287 A1 | 10/2004 | Swoyer et al. | |
| 2005/0131467 A1 | 6/2005 | Boveja | |
| 2005/0131486 A1 | 6/2005 | Boveja et al. | |
| 2005/0131487 A1 | 6/2005 | Boveja et al. | |
| 2005/0137644 A1 | 6/2005 | Boveja et al. | |
| 2005/0143787 A1 | 6/2005 | Boveja et al. | |
| 2005/0149146 A1 | 7/2005 | Boveja et al. | |
| 2005/0154425 A1 | 7/2005 | Boveja et al. | |
| 2005/0154426 A1 | 7/2005 | Boveja et al. | |
| 2005/0165458 A1 | 7/2005 | Boveja et al. | |
| 2005/0187590 A1 | 8/2005 | Boveja et al. | |
| 2005/0197678 A1 | 9/2005 | Boveja et al. | |
| 2005/0203584 A1 | 9/2005 | Twetan et al. | |
| 2005/0216070 A1 | 9/2005 | Boveja et al. | |
| 2005/0266301 A1 | 12/2005 | Smith et al. | |
| 2007/0060955 A1 | 3/2007 | Strother et al. | |
| 2007/0060968 A1 | 3/2007 | Strother et al. | |
| 2007/0060980 A1 | 3/2007 | Strother et al. | |
| 2007/0111587 A1 | 5/2007 | Ries et al. | |
| 2007/0265489 A1 | 11/2007 | Fowler et al. | |
| 2007/0270916 A1 | 11/2007 | Fischell et al. | |
| 2008/0039904 A1 | 2/2008 | Bulkes et al. | |
| 2008/0058901 A1 | 3/2008 | Ternes et al. | |
| 2008/0065182 A1 | 3/2008 | Strother et al. | |
| 2008/0077184 A1 | 3/2008 | Denker et al. | |
| 2008/0097554 A1 | 4/2008 | Payne et al. | |
| 2008/0255631 A1 | 10/2008 | Sjostedt et al. | |
| 2008/0262563 A1 | 10/2008 | Sjostedt | |
| 2009/0012576 A1 | 1/2009 | Erbstoeszer et al. | |
| 2009/0017700 A1 | 1/2009 | Zart et al. | |
| 2009/0018600 A1 | 1/2009 | Deininger et al. | |
| 2009/0018607 A1 | 1/2009 | Crowley et al. | |
| 2009/0132010 A1 | 5/2009 | Kronberg | |
| 2009/0157142 A1 | 6/2009 | Cauller | |
| 2009/0204173 A1 | 8/2009 | Fang et al. | |
| 2009/0248094 A1 | 10/2009 | McDonald | |
| 2009/0270948 A1 | 10/2009 | Nghiem et al. | |
| 2010/0038132 A1 | 2/2010 | Kinney et al. | |
| 2010/0049275 A1 | 2/2010 | Chavan et al. | |
| 2010/0106223 A1 | 4/2010 | Grevious et al. | |
| 2010/0137943 A1 | 6/2010 | Zhu | |
| 2010/0137944 A1 | 6/2010 | Zhu | |
| 2010/0168818 A1 | 7/2010 | Barror et al. | |
| 2010/0233896 A1 | 9/2010 | Dilmaghanian | |
| 2010/0305663 A1 | 12/2010 | Aghassian | |
| 2011/0112601 A1 | 5/2011 | Meadows et al. | |
| 2011/0144468 A1 | 6/2011 | Boggs et al. | |
| 2012/0315798 A1 | 12/2012 | Poon et al. | |
| 2013/0066399 A1 | 3/2013 | Min | |
| 2016/0114171 A1 | 4/2016 | Parker | |
| 2017/0036023 A1 | 2/2017 | Parker | |

OTHER PUBLICATIONS

Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.

North et al., "Spinal Cord Stimulation for Axial Low Back Pain," SPINE, vol. 30, No. 12, 2005, 7 pages.

(56) References Cited

OTHER PUBLICATIONS

North et al., "Spinal Cord Stimulation for Chronic, Intractable Pain: Experience over Two Decades," Neurosurgery, vol. 32, No. 2, Mar. 1993, 12 pages.
International Search Report and Written Opinion for International Application No. PCT/US2014/036576, Applicant: Nevro Corporation; dated Aug. 21, 2014, 7 pages.

* cited by examiner

Fig. 6C

MOLDED HEADERS FOR IMPLANTABLE SIGNAL GENERATORS, AND ASSOCIATED SYSTEMS AND METHODS

CROSS-REFERENCE TO RELATED APPLICATIONS

The present application is a continuation application of U.S. patent application Ser. No. 14/268,575, filed May 2, 2014, and titled "MOLDED HEADERS FOR IMPLANTABLE SIGNAL GENERATORS, AND ASSOCIATED SYSTEMS AND METHODS," which claims priority to U.S. Provisional Application No. 61/819,347, filed May 3, 2013, and titled MOLDED HEADERS FOR IMPLANTABLE SIGNAL GENERATORS, AND ASSOCIATED SYSTEMS AND METHODS. U.S. Provisional Application No. 61/819,347 is related to U.S. patent application Ser. No. 13/669,350, filed Nov. 5, 2012, and titled MEDICAL DEVICE COMMUNICATION AND CHARGING ASSEMBLIES FOR USE WITH IMPLANTABLE SIGNAL GENERATORS, AND ASSOCIATED SYSTEMS AND METHODS, which claims priority to U.S. Provisional Application 61/556,097, filed Nov. 4, 2011, and titled MEDICAL DEVICE COMMUNICATION AND CHARGING ASSEMBLIES FOR USE WITH IMPLANTABLE PULSE GENERATORS, AND ASSOCIATED SYSTEMS AND METHODS. The entirety of the above applications, and U.S. Design patent application Ser. No. 29/436,395, filed Nov. 5, 2012, and titled IMPLANTABLE SIGNAL GENERATOR, are incorporated by reference herein. To the extent the foregoing applications and/or any other materials incorporated herein by reference conflict with the present disclosure, the present disclosure controls.

TECHNICAL FIELD

The present technology is directed generally to molded headers, implantable signal generators having molded headers, and associated systems and methods. Molded headers in accordance with the present technology are suitable for securing and/or encapsulating one or more components of an implantable signal generator, including charging coils and communications antennas.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator (sometimes referred to as an "implantable pulse generator" or "IPG") that is operably coupled to one or more leads that deliver electrical signals or pulses to neurological tissue or muscle tissue. For example, several neurological stimulation systems for spinal cord stimulation (SCS) have cylindrical leads that include a lead body with a circular cross-sectional shape and multiple conductive rings spaced apart from each other at the distal end of the lead body. The conductive rings operate as individual electrodes or contacts to deliver electrical signals to the patient. The SCS leads are typically implanted either surgically or percutaneously through a needle inserted into the epidural space, often with the assistance of a stylet.

Once implanted, the signal generator applies electrical signals to the electrodes, which in turn modify the function of the patient's nervous system, such as by altering the patient's responsiveness to sensory stimuli and/or altering the patient's motor-circuit output. In particular, the electrical signals can generate sensations that mask or otherwise alter the patient's sensation of pain. For example, in many cases, patients report a tingling or paresthesia that is perceived as more pleasant and/or less uncomfortable than the underlying pain sensation. In other cases, the patients can report pain relief without paresthesia or other sensations. As used herein, unless explicitly stated otherwise, the terms "pulses" and "signals" are used interchangeably to include any waveform shapes, whether continuous or discontinuous, including but not limited to sinusoidal or non-sinusoidal waves such as square waves, triangle waves, sawtooth waves, etc.

Implantable signal generators generally include a communication antenna that allows operational parameters of a stimulation system to be altered, without necessitating a hard-wired external connection. Additionally, implantable signal generators often include a charging coil that allows a battery in the implantable signal generator to be recharged from an external power source. The design of the communication antenna and the charging coil, and their locations within the implantable signal generator, can significantly impact the performance of the stimulation system. If the antenna and/or the coil are poorly positioned or shielded, updating operational parameters and/or charging the implantable signal generator can be difficult or impossible. For example, in many existing systems it can be difficult for a patient or an operator to correctly position an external device to transmit signals to the implantable signal generator. Additionally, poor coil design or shielding interference can decrease the efficiency of the charging process and cause increased heating. Metal shells or casings that implantable signal generators often include can at least partially contribute to the effects described above. Positioning the communication antenna and/or charging coil outside of the casing can often partially alleviate some of these concerns. However, externally positioned components can increase the complexity and costs associated with the manufacturing of a device. Prior systems suffer from many of these and/or additional drawbacks.

DETAILED DESCRIPTION

The present technology is directed generally to communication and charging assemblies for medical devices, and more specifically to communication and charging assemblies for implantable neurological modulation systems. At least some embodiments of the present technology include implantable signal generators having a header configured to support communication antennas, charging coils and/or other components. The header can be constructed to support multiple components and provide for the manufacturing of implantable signal generators via procedures that, when compared to existing manufacturing techniques, reduce the associated complexity and/or costs. For example, headers in accordance with the present technology can facilitate simultaneously connecting multiple components to an implantable signal generator. Additionally, the reduced costs associated with the present technology can enable the economical production of implantable signal generators that provide improved, enhanced, more robust and/or more effective signal reception and/or generation, as well as enhanced charging efficiency and decreased heat generation.

Embodiments in accordance with the present technology can include devices, systems and associated methods that have different configurations, components, and/or procedures. Still other embodiments may eliminate particular components and/or procedures. The present technology, which includes associated devices, systems, and procedures, may include other embodiments with additional elements or steps, and/or may include other embodiments without several of the features or steps shown and described below with reference to FIGS. 1-6C. Several aspects of overall systems configured in accordance with the disclosed technology are described with reference to FIG. 1, and features specific to particular molded headers are then discussed with reference to FIGS. 2A-6C.

Figure 1:
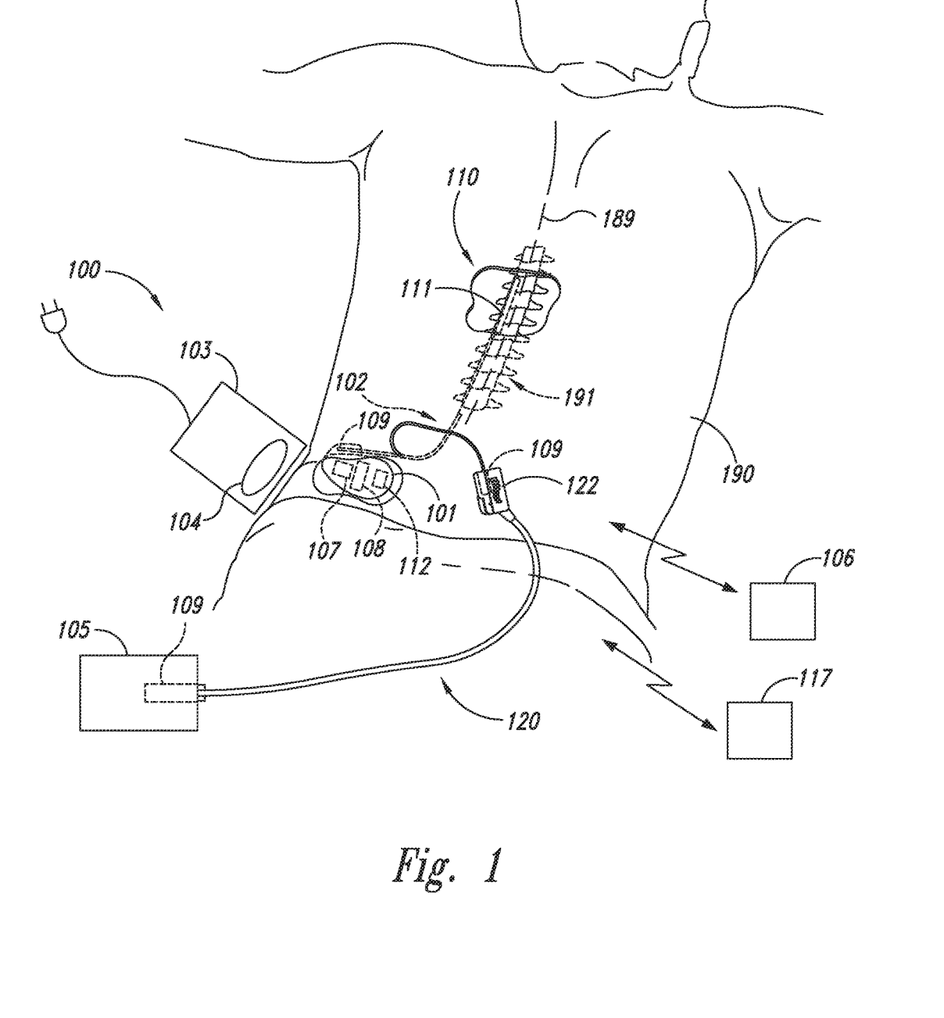
FIG. 1 is a partially schematic illustration of an implantable spinal cord modulation system positioned at a patient's spine to deliver therapeutic signals in accordance with an embodiment of the present technology.

FIG. 1 schematically illustrates a representative patient system 100 for providing relief from chronic pain and/or other conditions, arranged relative to the general anatomy of a patient's spinal cord 191. The overall patient system 100 can include a signal delivery device 110, which may be implanted within a patient 190, typically at or near the patient's spinal cord midline 189, and coupled to a signal generator 101 (e.g., a pulse generator). The signal delivery device 110 carries features for delivering therapy to the patient 190 after implantation. The signal generator 101 can be connected directly to the signal delivery device 110, or it can be coupled to the signal delivery device 110 via a signal link or lead extension 102. In a further representative embodiment, the signal delivery device 110 can include one or more elongated lead(s) or lead body or bodies 111. As used herein, the terms "lead" and "lead body" include any of a number of suitable substrates and/or support members that carry devices for providing therapy signals to the patient 190. For example, the lead or leads 111 can include one or more electrodes or electrical contacts that direct electrical signals into the patient's tissue, such as to provide for patient pain relief. In other embodiments, the signal delivery device 110 can include structures other than a lead body (e.g., a paddle) that also direct electrical signals and/or other types of signals to the patient 190.

The signal generator 101 can transmit signals (e.g., electrical signals or therapy signals) to the signal delivery device 110 that up-regulate (e.g., stimulate or excite) and/or down-regulate (e.g., block or suppress) target nerves. As used herein, and unless otherwise noted, to "modulate" or provide "modulation" to the target nerves refers generally to having either type of the foregoing effects on the target nerves. The signal generator 101 can include a machine-readable (e.g., computer-readable) medium containing instructions for generating and transmitting suitable therapy signals. The signal generator 101 and/or other elements of the system 100 can include one or more processor(s) 107, memory unit(s) 108 and/or input/output device(s) 112. Accordingly, the process of providing therapy signals, providing guidance information for positioning the signal delivery device(s) 110, and/or executing other associated functions can be performed by computer-executable instructions contained by computer-readable media located at the signal generator 101 and/or other system components. The signal generator 101 can include multiple portions, elements, and/or subsystems (e.g., for directing signals in accordance with multiple signal delivery parameters), carried in a single housing, as shown in FIG. 1, or in multiple housings.

In some embodiments, the signal generator 101 can obtain power to generate the therapy signals from an external power source 103. The external power source 103 can transmit power to the implanted signal generator 101 using electromagnetic induction (e.g., RF signals). For example, the external power source 103 can include an external coil 104 that communicates with a corresponding internal coil (not shown) within the implantable pulse generator 101. The external power source 103 can be portable for ease of use.

In the course of at least some overall procedures, an external stimulator or trial modulator 105 can be coupled to the signal delivery device 110 during an initial procedure, prior to implanting the signal generator 101. For example, a practitioner (e.g., a physician and/or a company representative) can use the trial modulator 105 to vary the therapy parameters provided to the signal delivery device 110 in real time, and select optimal or particularly efficacious parameters. These parameters can include the location from which the electrical signals are emitted, as well as the characteristics of the electrical signals provided to the signal delivery device 110. In a typical process, the practitioner uses a cable assembly 120 to temporarily connect the trial modulator 105 to the signal delivery device 110. The practitioner can test the efficacy of the signal delivery device 110 in an initial position. The practitioner can then disconnect the cable assembly 120 (e.g., at a connector 122), reposition the signal delivery device 110, and reapply the electrical therapy. This process can be performed iteratively until the practitioner obtains the desired position for the signal delivery device 110. Optionally, the practitioner may move the partially implanted signal delivery element 110 without disconnecting the cable assembly 120. In at least some embodiments, the iterative process of repositioning the signal delivery device 110 and/or varying the therapy parameters may be unnecessary and therefore eliminated.

The pulse generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. Receiving elements 109 can be at least generally similar in structure and function to those described in U.S. patent application Ser. No. 13/291,985, entitled MEDICAL DEVICE CONTACT ASSEMBLIES FOR USE WITH IMPLANTABLE LEADS, AND ASSOCIATED SYSTEMS AND METHODS, filed Nov. 8, 2011, which is incorporated by reference herein in its entirety.

After a trial period with the trial modulator 105, the practitioner can implant the implantable signal generator 101 within the patient 190 for longer term treatment. The signal delivery parameters provided by the signal generator 101 can still be updated after the signal generator 101 is implanted, via a wireless physician's programmer 117 (e.g., a physician's laptop, physician's remote, etc.) and/or a wireless patient programmer 106 (e.g., a patient's laptop, a patient's remote, etc.). Generally, the patient 190 has control over fewer parameters than does the practitioner.

Figure 2A:
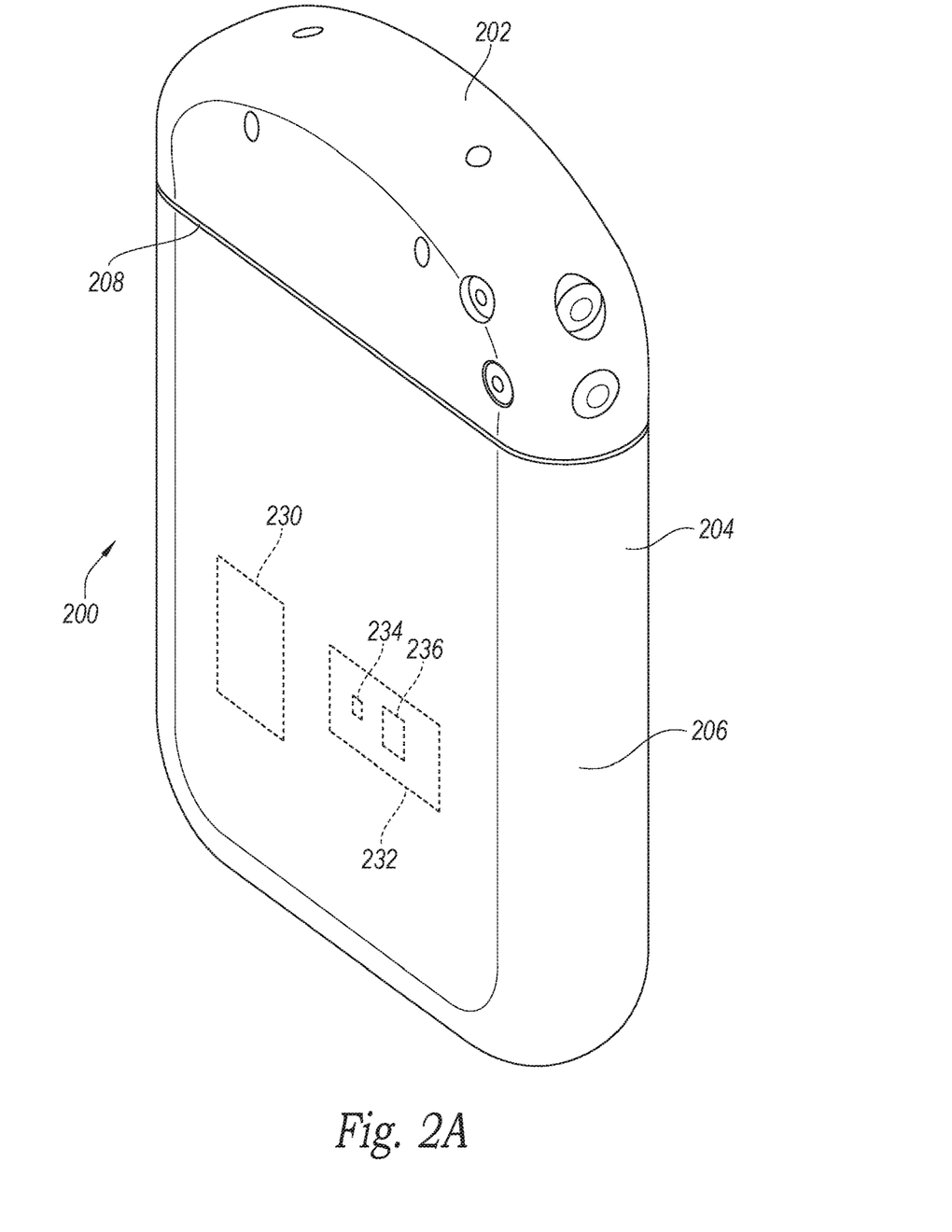
FIG. 2A is a partially schematic isometric view of an implantable signal generator having a molded header and a can configured in accordance with a further embodiment of the present technology.

FIG. 2A is a partially schematic isometric view of an implantable signal generator 200 having a molded header 202 and a can 204 configured in accordance with an embodiment of the present technology. Many of the embodiments described below include pre-formed or pre-molded headers having pre-formed openings in which a manufacturer can position one or more components. In other embodiments, headers can be formed in an in situ molding process that includes molding a header into a shape and simultaneously encasing components within the header during the molding process.

Figure 2B:
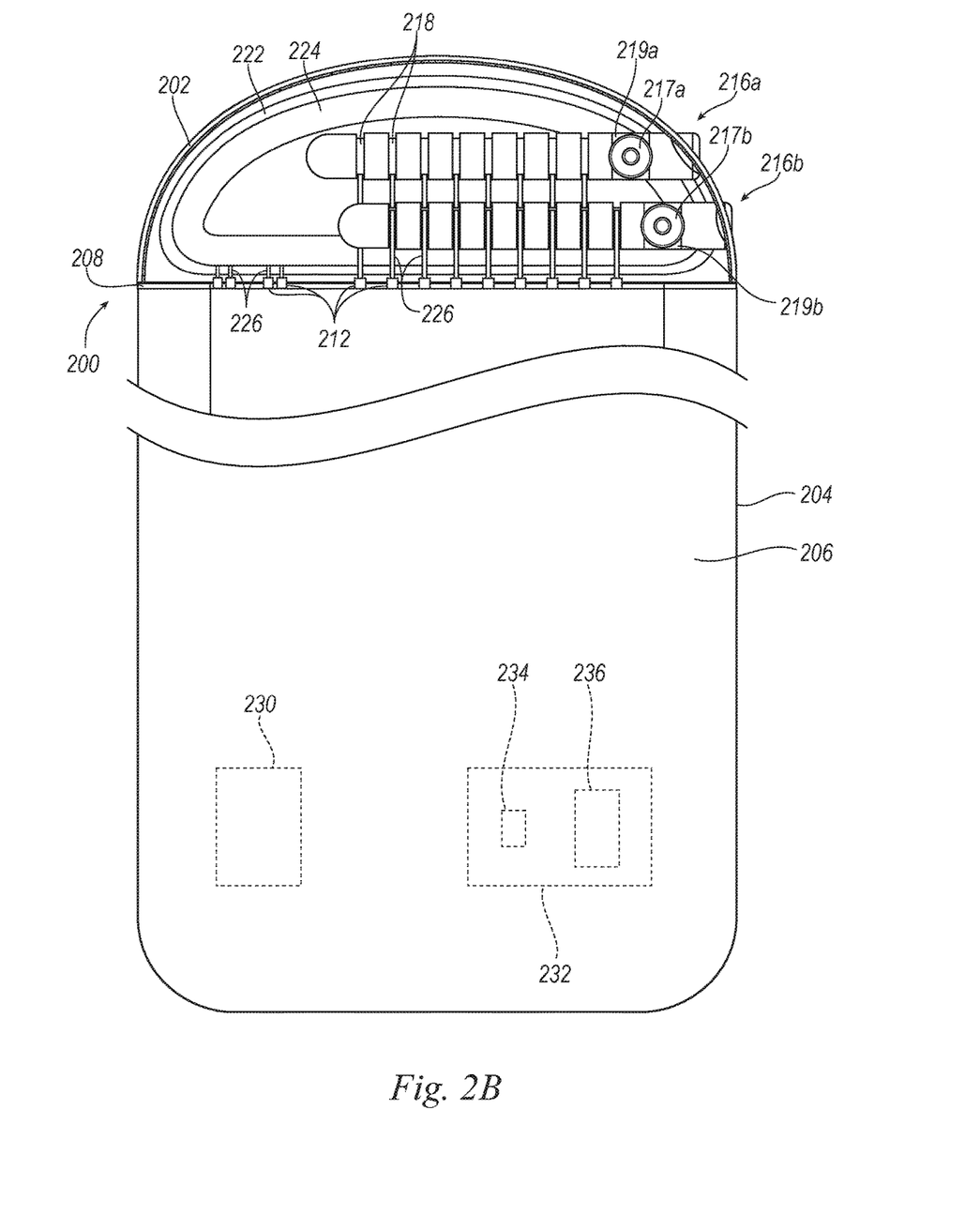
FIG. 2B is a partially cutaway side view of a portion of the implantable signal generator of FIG. 2A.

FIG. 2B is a partially cutaway side view of a portion of the implantable signal generator 200 of FIG. 2A. Referring to FIGS. 2A and 2B together, the can 204 may include a rounded rectangular shell 206 and an oval shaped lid 208 positioned at least partially between the header 202 and the can 204. In one embodiment, the shell 206 and the lid 208 can be titanium, and a weld joint can join the lid 208 to the shell 206. In other embodiments, the shell 206 and the lid 208 can be made of other metals or metal alloys, or plastic, and can be joined together by other methods including press fitting, adhesive materials and/or threaded connections. In any of these embodiments, the lid 208 can include a plurality of feed-throughs 212 for electrical communication between the header 202 and the can 204.

The molded header 202 can be formed from Tecothane®, Elast-Eon™, silicone, polymers, copolymers and/or any other suitable material, and can be attached to the can 204. The header 202 can house, support, and/or carry several components. For example, the molded header 202 can carry a charging coil 224, a communication antenna 222, a first receiving element 216a and a second receiving element 216b (collectively, receiving elements 216). These and several other components can be at least partially enclosed, encompassed, contained and/or otherwise positioned within the header in a variety of manners.

The receiving elements 216 can include a plurality of output terminals or contact assemblies 218, configured to provide electrical connections to the signal delivery device 110 (FIG. 1) or the lead extension 102 (FIG. 1). Additionally, a first set screw block 219a and a second set screw block 219b can be integral with or connected to the receiving elements 216a and 216b, respectively. The first set screw block 219a and the second set screw block 219b (collectively, set screw blocks 219) can provide for the securement of the signal delivery device 110 or the lead extension 102, as further described below. The communication antenna 222 and the charging coil 224 can be shaped, positioned, and/or otherwise configured to enhance the performance of the implantable signal generator 200, while fitting within the confines of the header 202 (as discussed in more detail in U.S. patent application Ser. No. 13/669,350, which was incorporated by reference above). Multiple wires 226 can extend upwardly from the can 204 through the feed-throughs 212 and couple to (a) individual contact assemblies 218, (b) the communication antenna 222, or (c) the charging coil 224.

The wires 226 can provide electrical connections between components within the header 202, e.g., the charging coil 224 and the communication antenna 222, and components within the can 204, e.g., a battery 230, a controller 232, etc. The battery 230 can be electrically coupled to the controller 232 and the output terminals or contact assemblies 218 to provide electrical power to the implantable signal generator 200 via the receiving elements 216. The battery 230 can be recharged via an electrical coupling to the charging coil 224. The controller 232 can be electrically coupled to the contact assemblies 218 and the battery 230, and can include a processor 234, memory 236, electronic circuitry, and other electronic components for controlling and/or operating the implantable signal generator 200. Computer readable instructions contained in the memory 236 can include operating parameters and instructions that can control the operation of the implantable signal generator 200. In operation, the charging coil 224 can convert electromagnetic energy (e.g., a magnetic flux) into electrical current to charge the battery 230. The communication antenna 222 can receive signals associated with operating and/or controlling the implantable signal generator 200. For example, control signals to update operating parameters (e.g., the frequency or duration of modulation signals) for the implantable signal generator 200 can be received by the communications antenna 222 and sent to the controller 232. The controller 232 can control the delivery of electrical power to the receiving elements 216.

The header 202 includes a first access seal 217a and a second access seal 217b (collectively referred to as the access seals 217). The access seals 217 include a self-sealing entrance point to provide access for a tool (e.g., a screwdriver) to secure a connection (e.g., a screw) to the signal delivery device 110 (FIG. 1) or the lead extension 102 (FIG. 1) via the set-screw blocks 219. The access seals 217 can be formed from a pliable silicone or other suitable material such that the tool can pass through and expand the entrance point. When the tool is withdrawn, the entrance point can automatically close to reduce or eliminate the possibility of any foreign material (e.g., blood or other bodily fluids) subsequently entering into the header 202.

The header 202 can be attached to the can 204 in a variety of suitable manners. For example, in one embodiment, the header 202 can be attached to the lid 208 (FIG. 2B) with an adhesive. In other embodiments, the lid 208, the can 204 and/or other components can include a groove, and the header 202 can include a ring that can engage the groove.

Figure 3A:
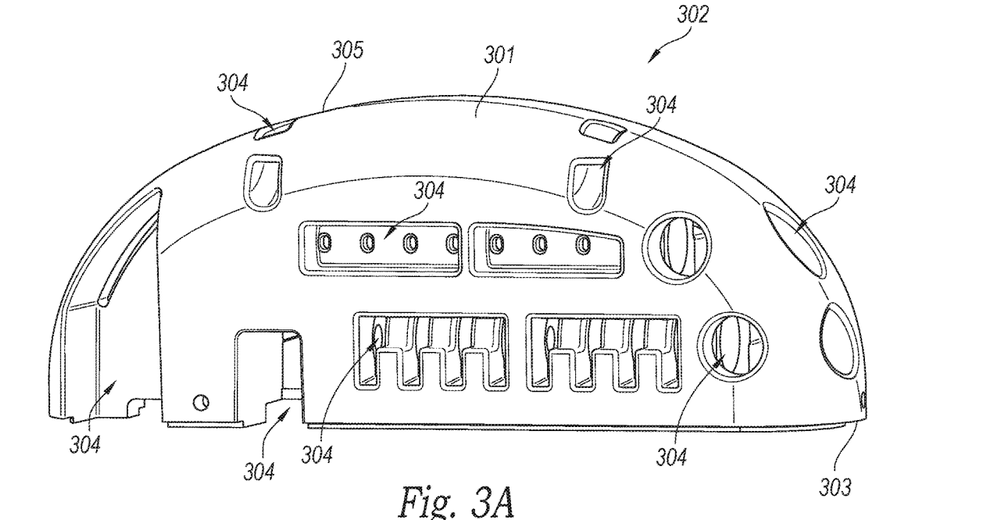
FIG. 3A is an isometric view of a molded header configured in accordance with an embodiment of the present technology.

FIG. 3A is an isometric view of a molded header 302 configured in accordance with an embodiment of the present technology. In the illustrated embodiment, a body 301 of the header 302 includes a curved or rounded upper surface 305, a base 303 and a plurality of cutouts or pre-formed openings 304. The openings 304 can be shaped to accommodate various components that can be positioned within the header 302 (e.g., receiving elements, charging coils, communication antennas, and/or other electronic, electrical or electromechanical components, etc.). The openings 304 can at least partially enclose, encompass and/or contain the components within the header 302. In several embodiments, components can be positioned within or at least partially within the header 302 and the header 302 can maintain the components in a desired position during subsequent attachment to the can 204. For example, the charging coil 224, the communication antenna 222 and/or the receiving elements 216 and the associated output terminals 218 can be received or positioned within the openings 304. The header 302 can help to align the wires 226 with the feed-throughs 212 (FIG. 2B), and/or align other connections or components of the can 204 with components positioned within the header 302. Maintaining the position of one or more components can reduce the complexity of the process for manufacturing the implantable signal generator 200, as described below. Additionally, the openings 304 can allow the manufacturer to precisely position the components within the header 302, which can provide several operational advantages for the implantable signal generator, as also described below.

Although the illustrated embodiments include wires 226 (FIG. 2B) that connect components in the header 202 or 302 with components in the can 204, components of the implantable signal generator 200 can be connected in a variety of suitable manners. For example, in some embodiments, the communication antenna 222, the charging coil 224, the receiving elements 216 and/or other components can include various wires, connectors, plugs and/or other features that provide for electrical coupling. In some embodiments, the components in the header 202 or 302 (e.g., the receiving elements 216, the charging coil 224 and the communication antenna 222) can include plugs that can be inserted into receptacles positioned on or attached to the lid 208.

In several embodiments, the header 302 can facilitate connecting multiple components in one step. For example, one method of manufacturing an implantable signal generator can include positioning multiple components in the openings 304 of the header 302 with multiple wires, connectors and/or plugs extending therefrom. The header 302 can subsequently be aligned with and brought together with the can 204 (FIGS. 2A and 2B), simultaneously establishing electrical connections between the components in the header 302 and components in the can 204 via connections with the multiple wires, connectors or plugs. In other embodiments, wires from more than one component can be carried by a single connector or plug that provides a connection between components in the header 202 or 302 and components in the can 204.

The molded headers 202 and 302 of FIGS. 2A-3B can be formed in a variety of manners. For example, a representative process includes constructing a mold having a desired header shape and injecting a liquid material into the mold, thereby forcing the liquid into the shape of the header. The liquid can be cured via cooling and/or other processes to form a solid header. A variety of molding techniques, including injection molding, compression molding, etc. can be used to mold the headers 202 and 302. In some embodiments, the molding process can include forming the openings 304, e.g., via mold inserts or other techniques. The openings 304 can also be formed after a header has been molded. For example, the openings 304 can be formed by cutting or otherwise removing material from a header 202 or 302. Additionally, the headers 202 and 302 can be formed to match the shape of at least a portion of the can 204, the shell 206 and/or the lid 208. For example, the molded headers 202 and 302 can include the oval shaped base 303 that matches and/or aligns with the shape of the can 202, the shell 206 and the lid 208.

Figure 3B:
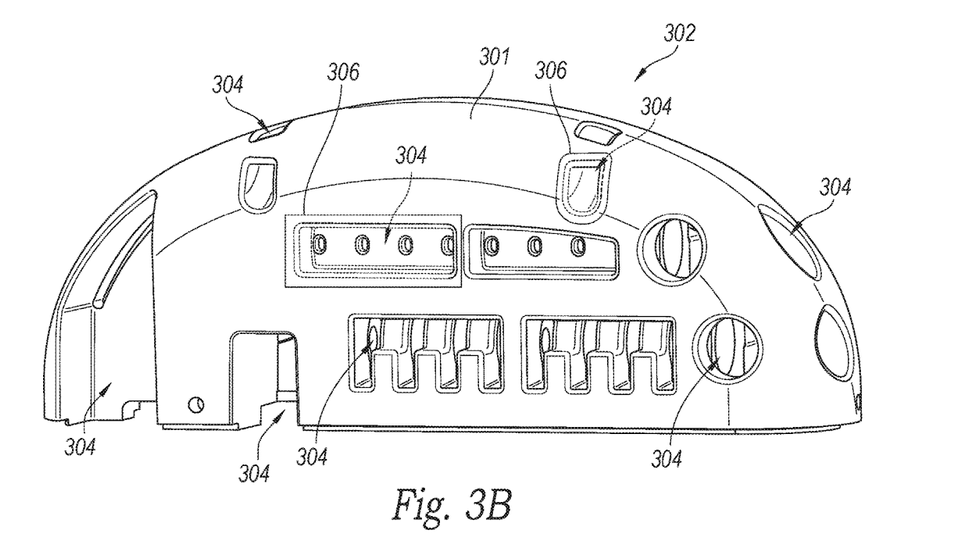
FIG. 3B is an isometric view of the header of FIG. 3A having multiple covers configured in accordance with an embodiment of the present technology.

FIG. 3B is an isometric view of the header 302 having multiple covers 306 configured in accordance with an embodiment of the present technology. In the illustrated embodiment, the covers 306 are positioned over two of the openings 304. Similar to the header 302, the covers 306 can be constructed from a variety of materials (e.g., Tecothane®, Elast-Eon™ silicone, polymers, copolymers and/or any other suitable material) and can cover or seal one or more of the openings 304. For example, in some embodiments, the covers 306 can be constructed of the same material as the header 302 and can be adhered to the header 302 via medical adhesive to cover or seal one or more of the openings 304. Although the illustrated embodiment includes covers that are positioned over the openings 304, in several embodiments, the covers 306 can be positioned partially or completely within the openings 304. The covers 306 can be coupled to the body 301 of the header 302 in various suitable manners. For example, thermal bonding, compression fitting and/or other techniques or procedures can adhere the covers 306 to the header 302. The covers 306 can be permanently attached to the header 302 to remain in position after implantation of an associated implantable signal generator and at least partially seal the header 302, reducing the likelihood of foreign material (e.g., blood or other bodily fluids) entering the header 302. The covers 306 can be applied to headers other than the header 302 shown in FIGS. 3A and 3B, e.g., the header 202 shown in FIGS. 2A and 2B and/or other headers described further below.

Figure 4:
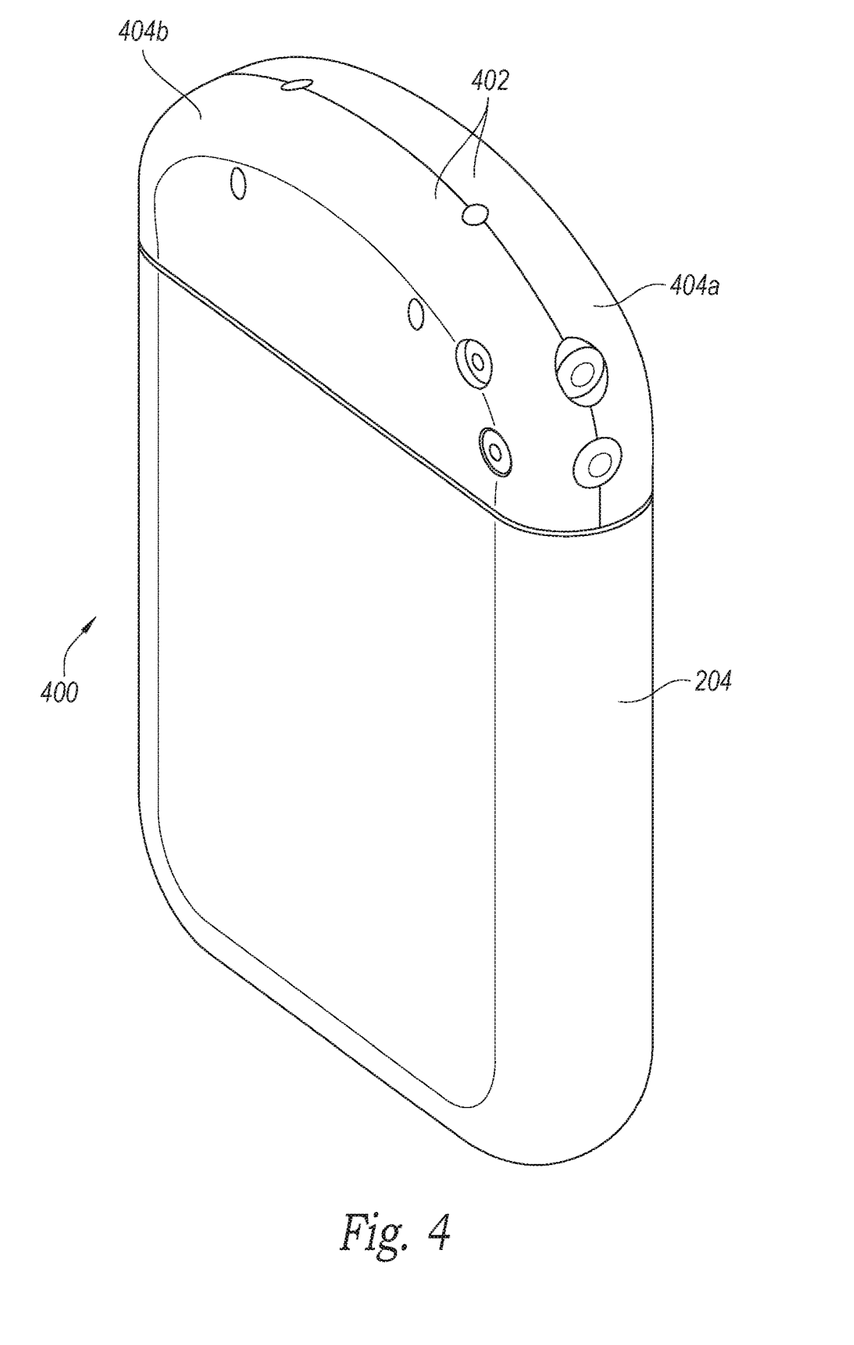
FIG. 4 is an isometric view of an implantable signal generator having a molded header configured in accordance with a further embodiment of the present technology.

FIG. 4 is an isometric view of an implantable signal generator 400 having a molded header 402 configured in accordance with an embodiment of the present technology. In the illustrated embodiment, the header 402 includes a first header portion 404a and a second header portion 404b (collectively, the header portions 404) that can be configured and joined in a clamshell arrangement. The header 402, overall, can be at least generally similar to the header 302 and can include multiple openings for receiving components. Similarly, the openings in the header 402 can be covered or sealed with covers (e.g., the covers 306 of FIG. 3B). Components (e.g., charging coils, communication antennas, receiving elements, etc.) can be positioned within the header 402 before or after the header portions 404 are coupled together. For example, in some embodiments, the header portions 404 can be joined together and components can then be positioned therein in a manner at least generally similar to that described above with respect to the header 302.

In other embodiments, components can be positioned within the header 402 as the coupleable header portions 404 are joined together. For example, the header portions 404 can be brought together to capture and/or at least partially surround the receiving elements 216 (FIG. 2A) and/or other components. Furthermore, the header portions 404 can be joined together before or after the header 402 is coupled to the can 204. For example, the first header portion 404a can be coupled to the can 204 first, and the second header portion 404b can be subsequently coupled to both the can 204 and the first header portion 404a. The header portions 404 can be coupled or joined together in a variety of suitable manners or techniques. For example, thermal bonding, medical adhesive and/or other suitable materials, processes and/or methods may be used to join the header portions 404.

Figure 5A:
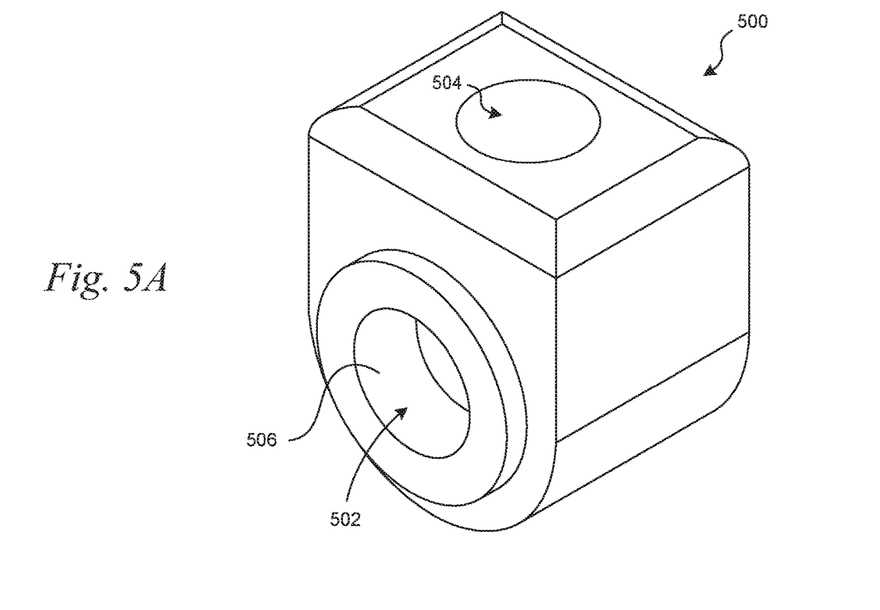
FIGS. 5A and 5B are isometric and cross sectional side views, respectively, of a set screw block configured in accordance with another embodiment of the present technology.
Figure 5B:
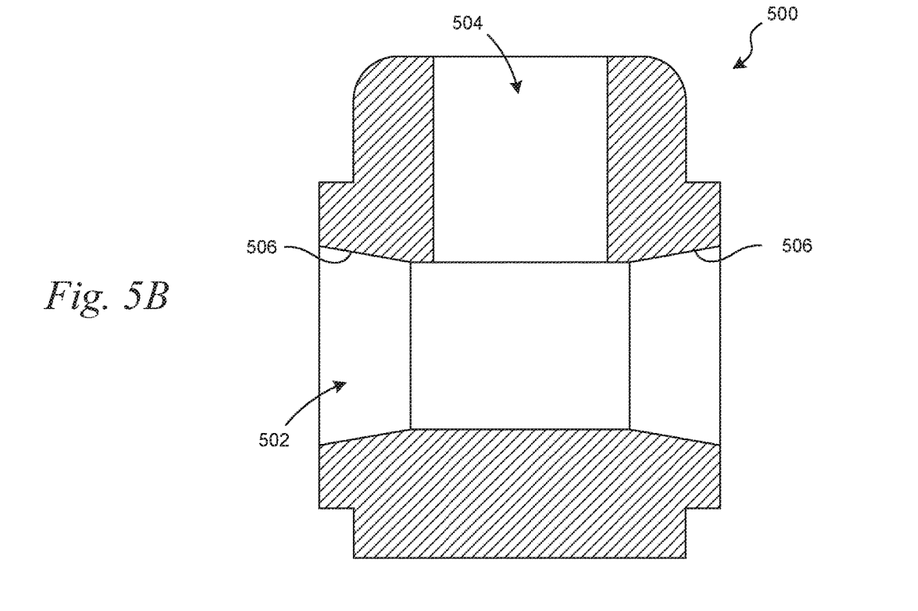

FIG. 5A is an isometric view of a set screw block 500 configured in accordance with an embodiment of the present technology. Similar to the set screw blocks 219 described above with respect to FIG. 2B, the set screw block 500 can be integral with or connected to an output terminal or receiving element (e.g., the receiving elements 216). FIG. 5B is a cross-sectional side view of the set screw block 500. Referring to FIGS. 5A and 5B together, the set screw block 500 includes a receiving passage 502 and a fastener conduit 504. The receiving passage 502 includes a funnel shaped, tapered sidewall 506. The receiving passage 502 can receive an electrical connector or plug that is integral with or connected to a proximal end of one of the components of the patient system 100 described above with reference to FIG. 1. For example, the plug can be integral with any of the signal delivery devices 110 described above, e.g., the leads 111. The plug can facilitate an electrical connection between the leads 111 and the implantable signal generators 200 and 400. In several embodiments, the receiving elements can receive plugs or conductor assemblies that are at least generally similar to those described in U.S. patent application Ser. No. 13/291,985 which, as described above, is incorporated by reference herein.

The funnel shaped sidewall 506 of the set screw block 500 can facilitate insertion of plugs or conductor assemblies. For example, a practitioner is not required to ensure perfect alignment of a plug with the receiving passage 502. Rather, as the practitioner inserts the plug into the receiving passage 502, the funnel shaped sidewall 506 can engage the plug and guide the plug to the center of the receiving passage 502.

The fastener conduit 504 can receive a variety of fasteners to secure a plug of conductor assembly within the set screw block 500. For example, the fastener conduit 504 can receive a screw that can engage a plug within the receiving passage 502, removably securing the plug within a receiving element. In some embodiments, the fastener conduit 504 can include threads (not shown) to engage set screws or other fasteners. In the illustrated embodiment, the fastener conduit 504 does not include threads, and the set screw can include threads that engage corresponding threads on a plug positioned within the receiving passage 502. In several embodiments, the fastener conduit 504 can receive other fasteners to secure plugs. For example, press-fit plugs or other components can be positioned within the fastener conduit 504 to secure a plug.

Figure 6A:
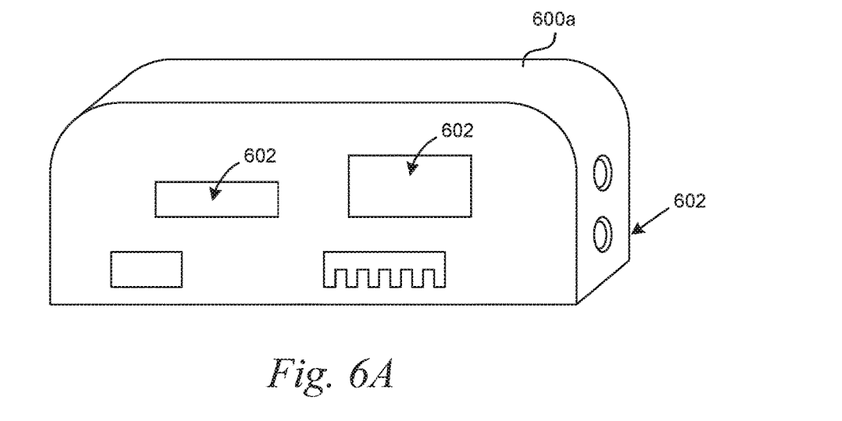
FIGS. 6A-6C are isometric views of molded headers configured in accordance with embodiments of the present technology.
Figure 6B:
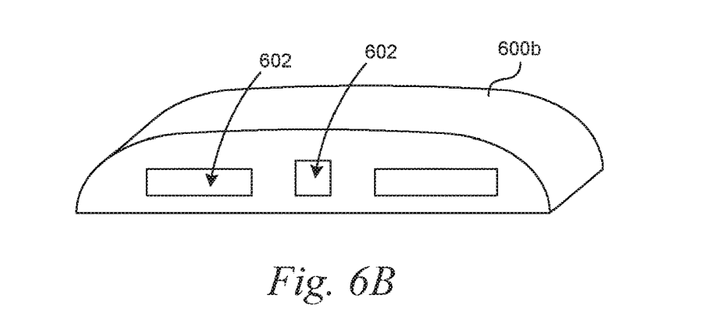
Figure 6C:
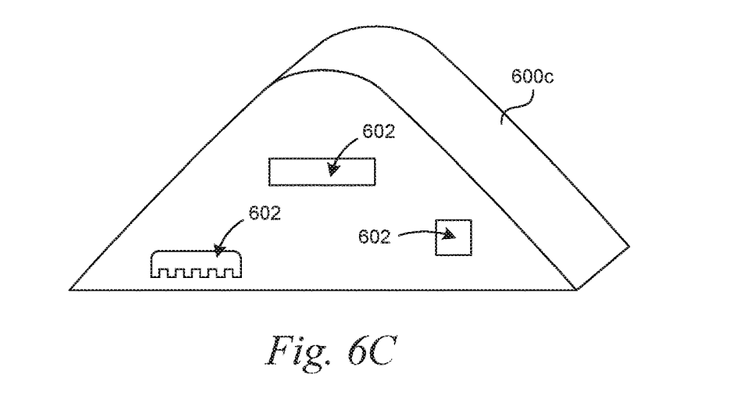

Molded headers in accordance with the present technology can have a variety of suitable shapes and configurations. FIGS. 6A, 6B and 6C are isometric views of molded headers 600a, 600b and 600c, respectively, configured in accordance with embodiments of the present technology. In the illustrated embodiment of FIG. 6A, the molded header 600a has a rounded rectangular shape. The molded header 600b of FIG. 6B has a curved shape with a low profile, while the molded header 600c of FIG. 6C includes a triangular shape. Similar to the molded headers 202, 302 and 402 described above, the molded headers 600a-600c can include one or more openings 602 positioned to receive various components. While the shapes and the various openings 602 of the headers 600a-600c represent particular embodiments of the present technology, numerous additional headers having shapes and/or openings that differ from the illustrated embodiments are within the scope of the present disclosure.

Embodiments in accordance with the present technology can provide several advantages over existing devices. For example, as described above with reference to FIGS. 3A and 3B, the pre-formed openings 304 can enable the components to be precisely positioned within an implantable signal generator. This precise positioning can produce increased performance by reducing the likelihood of electrical shorts and/or other damage resulting from inadvertent contact between components, thereby improving the reliability of the implantable signal generator. Additionally, the precisely positioned components of the present technology can reduce electromagnetic interference, shielding and/or other detrimental effects. Furthermore, positioning components within the pre-formed openings 304 can enable more components to be positioned outside of the implantable signal generator, thereby providing for advanced designs and enhanced capabilities. For example, the openings 304 can enable a variety of designs that position components in various three dimensional spatial relationships to each other within a header. In several embodiments, components can be stacked, staggered, or otherwise positioned to increase the number of components within a header.

In addition to the advantages discussed above, implantable signal generators and/or molded headers in accordance with the present technology can be particularly beneficial for systems employing high frequency modulation. For example, the signals and operational parameters of high frequency systems can require greater power usage than traditional SCS systems. The increased charging efficiency of implantable signal generators having charging coils positioned within a header can help meet greater power requirements without necessitating longer charge times (as described in U.S. patent application Ser. No. 13/669,350, of which the present application is a continuation-in-part). The technology described herein can reduce the manufacturing complexity and costs of such implantable signal generators, facilitating the economical production of these devices. Accordingly, several embodiments in accordance with the present technology can be combined with high frequency modulation systems, including those described in U.S. patent application Ser. No. 12/264,836, filed Nov. 4, 2008, and titled MULTI-FREQUENCY NEURAL TREATMENTS AND ASSOCIATED SYSTEMS AND METHODS; U.S. patent application Ser. No. 12/765,747, filed Apr. 22, 2010, and titled SELECTIVE HIGH-FREQUENCY SPINAL CORD MODULATION FOR INHIBITING PAIN WITH REDUCED SIDE EFFECTS AND ASSOCIATED SYSTEMS AND METHODS; and U.S. patent application Ser. No. 13/607,617, filed Sep. 7, 2012, and titled SELECTIVE HIGH FREQUENCY SPINAL CORD MODULATION FOR INHIBITING PAIN, INCLUDING CEPHALIC AND/OR TOTAL BODY PAIN WITH REDUCED SIDE EFFECTS, AND ASSOCIATED SYSTEMS AND METHODS. The above referenced patent applications are incorporated herein by reference in their entireties.

From the foregoing, it will be appreciated that specific embodiments of the disclosed technology have been described herein for purposes of illustration, but that various modifications may be made without deviating from the technology. For example, in addition to, or in lieu of, an adhesive or a ring and groove arrangement that can secure a header to a can, a header can include a portion that can at least partially extend into the shell. In one embodiment, the lid can be positioned below the opening of the can, and a portion of the header can be received within the resulting space. Additionally, although the embodiment of FIG. 4 describes a header 402 having two header portions 404, other headers in accordance with the present technology can include additional header portions. Other materials may be used in place of those described herein, or additional components may be added or removed. For example, although the illustrated embodiments include a header having two receiving elements, other embodiments can include additional receiving elements, or other connectors. Additionally, any of the embodiments shown or described herein may be combined with each other as the context permits.

REPRESENTATIVE EMBODIMENTS

In one embodiment, there is provided an implantable signal generator, comprising: (a) a can having a shell and a battery positioned at least partially within the shell; (b) an output terminal operably coupled to the battery and positioned to provide electrical power to a signal delivery device; and (c) a pre-molded header coupled to the can and having a plurality of openings, wherein the output terminal is positioned at least partially within an individual opening. The pre-molded header of the implantable signal generator can comprise a polymer. The pre-molded header can also comprise a first header portion and a second header portion, wherein the first and second header portions are coupleable to form the pre-molded header.

The implantable signal generator can further comprise a cover positioned over at least one of the plurality of openings to at least partially seal the pre-molded header. A set screw block can be positioned at least partially within the pre-molded header, and the set screw block can include a receiving passage having a funnel shaped sidewall. An access seal can be positioned to provide access to the set screw block.

The individual opening can be a first individual opening, and the implantable signal generator can further comprise: (d) a charging coil; and (e) a communication antenna. The charging coil can be operably coupled to the battery and positioned at least partially within a second individual opening. The communication antenna can be positioned at least partially within a third individual opening to receive control signals.

The implantable signal generator can further comprise a charging coil positioned within the pre-molded header, wherein the pre-molded header includes a curved surface, and wherein the charging coil is shaped to at least partially match the curved surface.

In another embodiment, there is provided a pre-molded header for an implantable signal generator. The pre-molded header comprises: (a) a body having a rounded upper surface and a base shaped to align with a shell of the implantable signal generator; and (b) an opening positioned to contain an electrical component. The opening can be a first opening shaped to receive a charging coil, and the pre-molded header can further comprise a second opening shaped to receive a communication antenna. The body of the pre-molded header can comprise a polymer. The pre-molded header can include a cover affixed to the body over the opening. The electrical component can comprise a charging coil shaped to match the rounded upper surface.

In yet another embodiment, there is provided a method for forming an implantable signal generator, comprising: (a) inserting an electronic component at least partially within a pre-formed opening in a pre-molded header; and (b) attaching the pre-molded header to a can having a shell and a lid. Inserting an electronic component at least partially within the pre-formed opening can include inserting a charging coil at least partially within the pre-formed opening, prior to attaching the pre-molded header to the can. The method can further comprise positioning a battery within the can, and attaching the pre-molded header to the can may include aligning the header with the can and establishing an electrical connection between the charging coil and the battery.

The electronic component can be a charging coil shaped to at least partially match a rounded upper surface of the pre-molded header, and inserting an electronic component at least partially within the pre-formed opening can include inserting the charging coil at least partially within the pre-formed opening.

The method may further comprise: attaching a cover to the pre-molded header to seal the pre-formed opening; positioning a communication antenna at least partially within a second pre-formed opening, prior to attaching the pre-molded header to the can; and/or positioning a set screw block at least partially within the pre-molded header to receive an electrical connector, wherein the set screw block includes a receiving passage having a tapered sidewall.

In another embodiment, there is provided a method for forming a pre-molded header for an implantable signal generator having a can. The method can comprise forming a body having a plurality of openings positioned to receive electronic components and a base shaped to at least partially match a shape of the can. Forming the body can include forming an external shape of the body using a molding process. Forming the pre-molded header can further include: forming the body to include a rounded upper surface; and/or forming the body to include an opening shaped to receive a charging coil having a shape that at least partially matches the rounded upper surface. Forming the body can include: forming the plurality of openings as part of the molding process; forming the plurality of openings after the molding process; and/or forming a first individual opening as part of the molding process and forming a second individual opening after the molding process. The method may comprise providing a cover shaped to affix to the body and seal an individual opening.

While various advantages and features associated with certain embodiments have been described above in the context of those embodiments, other embodiments may also exhibit such advantages and/or features, and not all embodiments need necessarily exhibit such advantages and/or features to fall within the scope of the technology. Accordingly, the disclosure and associated technology can encompass other embodiments not expressly shown or described herein.

We claim:
1. An implantable signal generator, comprising:
   a can;
   a pre-molded header coupled to the can and having a first opening, a second opening transversely intersecting the first opening, and a third opening;
   an elongate receiving element having a plurality of output terminals disposed at least partially within the first opening, wherein at least one of the plurality of output terminals are accessible through the second opening; and
   a charging coil positioned in the third opening.
2. The implantable signal generator of claim 1 wherein the pre-molded header further includes a fourth opening, the implantable signal generator further comprising:
   a first cover sealing the third opening;
   a communication antenna positioned in the fourth opening; and
   a second cover sealing the fourth opening.
3. The implantable signal generator of claim 1 wherein the pre-molded header further includes a fourth opening shaped to receive a communication antenna.
4. The implantable signal generator of claim 1, further comprising:
   a battery positioned in the can; and
   wherein the charging coil is electrically coupled to the battery via a wire extending from the charging coil and passing through the pre-molded header.
5. The implantable signal generator of claim 4 wherein the wire is a first wire, wherein the pre-molded header further includes a fourth opening, and wherein the implantable signal generator further comprises:
   a first cover sealing the third opening
   a controller positioned in the can;

a communication antenna positioned in the fourth opening, wherein the communication antenna is electrically coupled to the controller via a second wire, and wherein the second wire extends from the communication antenna and passes through the pre-molded header; and a second cover sealing the fourth opening.

6. The implantable signal generator of claim 1, further comprising:

a set screw block positioned proximate the elongate receiving element to removably secure a signal delivery device to the implantable signal generator, wherein the set screw block includes a funnel shaped sidewall.

7. The implantable signal generator of claim 6 wherein the pre-molded header includes an access seal positioned to provide self-sealing access to the set screw block.

8. An implantable signal generator, comprising:

a can;

a pre-molded header coupled to the can and having a first opening, a second opening transversely intersecting the first opening, and a third opening;

an elongate receiving element having a plurality of output terminals disposed at least partially within the first opening, wherein at least one of the plurality of output terminals are accessible through the second opening;

a charging coil positioned in the third opening; and a set screw block positioned at least partially within the pre-molded header, the set screw block including a receiving passage having a tapered sidewall.

9. The implantable signal generator of claim 8, wherein the receiving element having a plurality of output terminals is positioned to provide electrical connections to a signal delivery device, and wherein the set screw block is positioned to removably secure the signal delivery device to the receiving element.

10. The implantable signal generator of claim 9 wherein the pre-molded header includes an access seal positioned to provide self-sealing access to the set screw block.

11. The implantable signal generator of claim 8 wherein the pre-molded header includes an external surface having a rounded shape, and wherein the charging coil is shaped to match the rounded shape of the external surface.

12. An implantable signal generator component, comprising:

a pre-molded header having a first opening, a second opening transversely intersecting the first opening, and a third opening;

an elongate receiving element having a plurality of output terminals disposed at least partially within the first opening, wherein at least one of the plurality of output terminals are accessible through the second opening; and a charging coil positioned in the third opening.

13. An implantable signal generator, comprising:

a can;

a pre-molded header coupled to the can and having a first opening, a second opening transversely intersecting the first opening, a third opening shaped to receive a charging coil, and a fourth opening shaped to receive a communication antenna; and an elongate receiving element having a plurality of output terminals disposed at least partially within the first opening, wherein at least one of the plurality of output terminals are accessible through the second opening.

\* \* \* \* \*

UNITED STATES PATENT AND TRADEMARK OFFICE
CERTIFICATE OF CORRECTION

PATENT NO. : 10,065,044 B2
APPLICATION NO. : 14/981463
DATED : September 4, 2018
INVENTOR(S) : Vivek Sharma et al.

Page 1 of 1

It is certified that error appears in the above-identified patent and that said Letters Patent is hereby corrected as shown below:

In the Specification

In Column 2, Line 64, delete "cross sectional" and insert -- cross-sectional --, therefor.

Signed and Sealed this
Twenty-fifth Day of December, 2018

Andrei Iancu
*Director of the United States Patent and Trademark Office*